US010492726B2

United States Patent
Dusan et al.

(10) Patent No.: US 10,492,726 B2
(45) Date of Patent: Dec. 3, 2019

(54) WEARING DEPENDENT OPERATION OF WEARABLE DEVICE

(71) Applicant: Apple Inc., Cupertino, CA (US)

(72) Inventors: Sorin V. Dusan, Cupertino, CA (US); Daniel J. Culbert, Cupertino, CA (US); Todd K. Whitehurst, Cupertino, CA (US)

(73) Assignee: Apple Inc., Cupenino, CA (US)

( * ) Notice: Subject to any disclaimer, the term of this patent is extended or adjusted under 35 U.S.C. 154(b) by 168 days.

(21) Appl. No.: 15/115,474

(22) PCT Filed: Jan. 31, 2014

(86) PCT No.: PCT/US2014/014151
§ 371 (c)(1),
(2) Date: Jul. 29, 2016

(87) PCT Pub. No.: WO2015/116163
PCT Pub. Date: Aug. 6, 2015

(65) Prior Publication Data
US 2017/0007183 A1    Jan. 12, 2017

(51) Int. Cl.
*A61B 5/08*   (2006.01)
*A61B 5/00*   (2006.01)
(Continued)

(52) U.S. Cl.
CPC ........ *A61B 5/6831* (2013.01); *A61B 5/02416* (2013.01); *A61B 5/0402* (2013.01);
(Continued)

(58) Field of Classification Search
CPC . A61B 5/0205; A61B 5/02416; A61B 5/6831; A61B 5/6844
See application file for complete search history.

(56) References Cited

U.S. PATENT DOCUMENTS 4,951,679 A * 8/1990 Harada ................. A61B 5/022
600/485
2003/0173408 A1 9/2003 Mosher et al.
(Continued)

FOREIGN PATENT DOCUMENTS

| CN | 1406554 | 4/2003 |
| CN | 1572252 | 2/2005 |

(Continued)

OTHER PUBLICATIONS

International Search Report and Written Opinion dated Nov. 10, 2014, US/PCT/2014/014151, 11 pages.

*Primary Examiner* — Michael J D Abreu
(74) *Attorney, Agent, or Firm* — Brownstein Hyatt Farber Schreck, LLP

(57) ABSTRACT

A wearable device that attaches to a body part of a user via an attachment member operates in at least a connected and a disconnected state. One or more sensors located in the wearable device and/or the attachment member detect the user's body part when present. Such detection may only be performed when the attachment member is in a connected configuration and may be used to switch the wearable device between the connected and disconnected states. In this way, the wearable device operates in the connected state when worn by a user and in the disconnected state when not worn by the user.

21 Claims, 10 Drawing Sheets

(51) Int. Cl.
   *A61B 5/024*   (2006.01)
   *A61B 5/0402*  (2006.01)
   *A61B 5/053*   (2006.01)

(52) U.S. Cl.
   CPC .......... *A61B 5/0533* (2013.01); *A61B 5/6824* (2013.01); *A61B 5/6844* (2013.01); *A61B 2560/0266* (2013.01)

(56) References Cited

U.S. PATENT DOCUMENTS

| | | | |
|---|---|---|---|
| 2005/0020927 A1 | 1/2005 | Blondeau et al. | |
| 2006/0011729 A1 | 1/2006 | Sarela et al. | |
| 2008/0058783 A1* | 3/2008 | Altshuler | A61B 18/203 606/9 |
| 2009/0216182 A1* | 8/2009 | Lauchard | A61M 5/20 604/65 |
| 2012/0105225 A1 | 5/2012 | Valtonen | |
| 2014/0070957 A1* | 3/2014 | Longinotti-Buitoni | A61B 5/02055 340/870.01 |
| 2014/0114167 A1* | 4/2014 | Reaser, Jr. | A61B 5/046 600/393 |
| 2015/0031964 A1* | 1/2015 | Bly | G16H 40/67 600/301 |

FOREIGN PATENT DOCUMENTS

| | | |
|---|---|---|
| CN | 1843288 | 10/2006 |
| CN | 101647702 | 2/2010 |
| CN | 103445777 | 12/2013 |
| CN | 103536279 | 1/2014 |
| DE | 102009003416 | 8/2010 |
| EP | 1615187 | 1/2006 |
| JP | 2008073462 | 4/2008 |
| KR | 20040089728 | 10/2004 |

* cited by examiner

WEARING DEPENDENT OPERATION OF WEARABLE DEVICE

CROSS REFERENCE TO RELATED APPLICATION

This application is a 35 U.S.C. § 371 application of PCT/US2014/014151, filed on Jan. 31, 2014, and entitled "Wearing Dependent Operation of Wearable Device," which is incorporated by reference as if fully disclosed herein.

TECHNICAL FIELD

This disclosure relates generally to wearable devices, and more specifically to changing operation of a wearable device when worn, versus when not worn.

BACKGROUND

Wearable devices, such as heart rate or other fitness monitors, may be operable in connected and disconnected states. The connected state may be for operation when the wearable device is worn by a user. Similarly, the disconnected state may be for operation when the wearable device is not worn by a user. The disconnected state may permit download or display of data, user input and the like, but may not provide active monitoring functions that are provided while being worn, as one example.

In the connected state, a wearable device such as heart rate monitor based on photoplethysmographic sensors or electrocardiographic sensors may be operable to detect and monitor the user's heart rate and/or similar operations that require the user to be wearing the wearable device. In the disconnected state, such a wearable device may be configured by the user and/or perform other operations that do not require the user to be wearing the wearable device.

In order for such a wearable device to operate properly in either the connected or disconnected state, the wearable device may need to be aware which state it should be operating in. This may require the wearable device to be aware or sense whether or not the user is currently wearing the wearable device. In some cases, a user may enter input (such as via a touch screen, one or more buttons, and/or one or more other input/output mechanisms) to indicate to the wearable device whether the user is currently wearing the wearable device or not. However, requiring the user to enter input to change the state of the wearable device may be inconvenient and/or burdensome.

SUMMARY

The present disclosure discloses systems, apparatuses, and methods for operating a wearable device dependent on whether or not the wearable device is worn. A wearable device that attaches to a body part of a user via an attachment member may operate in at least a connected and a disconnected state. One or more sensors located in the wearable device and/or the attachment member may detect when the device is attached to or in a close proximity of an object. One or more sensors located in the wearable device and/or the attachment member may detect that the object attached to is the user's body part when present. Such combined/double detection may be used, in some cases with other data, to switch the wearable device between the connected and disconnected states.

Additionally, the attachment member may have a connected configuration where the attachment member attaches the wearable device to the user's body part and a disconnected configuration where the attachment member may not attach the wearable device to the user's body part. In some implementations, the configuration of the attachment member may be detected and the sensor may determine whether or not the user's body part is detected when the attachment member transitions from the disconnected to the connected configuration in order to switch the state of the wearable device from disconnected to connected. Similarly, if the wearable device is operating in the connected state and the attachment member transitions from the connected configuration to the disconnected configuration, the wearable device may switch to the disconnected state.

In various cases, determination that the attachment member has transitioned between the connected and disconnected configurations may be performed based on measured conductance between two or more contacts located in the wearable device and/or the attachment member that are conductively connected in the connected configuration and not conductively connected in the disconnected configuration. In other cases, the attachment member or the wearable device may include a proximity sensor which may be utilized to determine when the device and the attachment member have transitioned between connected and disconnected configurations. In still other cases, the attachment member may include multiple portions that are coupleable to each other utilizing two or more magnetic elements and a hall effect sensor may be utilized to determine when the magnetic elements are attracting each other, and thus coupling the portions in the connected configuration. In still other cases, the attachment member may include a single portion that may be stretched in response to applied force and multiple capacitive elements that are relatively closer to each other when the attachment member is unstretched and further from each other when the attachment member is stretched, thus altering the capacitance between the capacitive elements. As such, the attachment member may be in the connected or disconnected configuration when unstretched and the exact configuration that the attachment member is in may be the reverse of the configuration the attachment member was in before the attachment member was last stretched.

In various implementations, the wearable device may authenticate the user while operating in the connected state. In such cases, the wearable device may determine that the user is no longer authenticated when switching to the disconnected state.

In one or more implementations, a system for operating a wearable device dependent on whether or not the wearable device is worn may include a wearable device that operates in at least a connected and a disconnected state; at least one attachment member that attaches the wearable device to at least one body part of at least one user; and at least one sensor that detects the at least one body part of the at least one user. The wearable device may switch from the disconnected state to the connected state based at least on detection of the at least one body part of the at least one user.

In some implementations, a wearable device may include at least one processing unit that operates in at least a connected and a disconnected state; at least one attachment member that attaches the at least one processing unit to at least one body part of at least one user; and at least one sensor that detects the at least one body part of the at least one user. The at least one processing unit may switch from the disconnected state to the connected state based at least on detection of the at least one body part of the at least one user.

In various implementations, a method for operating a wearable device dependent on whether or not the wearable device is worn may include if a wearable device is operating in a disconnected state, determining to switch to a connected state by: detecting that at least one attachment member that attaches the wearable device to at least one body part of at least one user has been transitioned from a disconnected configuration to a connected configuration and upon detecting that the at least one attachment member has been transitioned from the disconnected configuration to the connected configuration, detecting the at least one body part of the at least one user utilizing at least one sensor.

It is to be understood that both the foregoing general description and the following detailed description are for purposes of example and explanation and do not necessarily limit the present disclosure. The accompanying drawings, which are incorporated in and constitute a part of the specification, illustrate subject matter of the disclosure. Together, the descriptions and the drawings serve to explain the principles of the disclosure.

DETAILED DESCRIPTION

Figure 1:
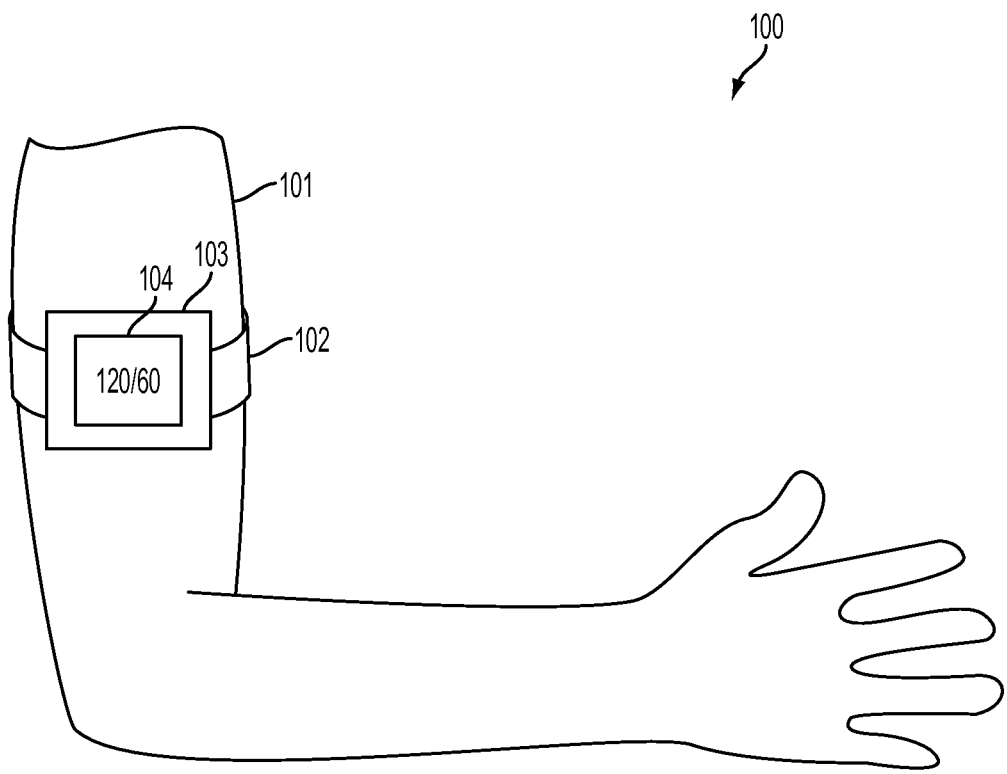
FIG. 1 is an isometric view of a system for operating a wearable device dependent on whether or not the wearable device is worn.

The description that follows includes sample systems, methods, and computer program products that embody various elements of the present disclosure. However, it should be understood that the described disclosure may be practiced in a variety of forms in addition to those described herein.

The present disclosure discloses systems, apparatuses, and methods for operating a wearable device dependent on whether or not the wearable device is worn. A wearable device (such as a heart rate monitor, blood pressure monitor, fitness monitor, or other wearable device) that attaches to a body part of a user (such as a bicep, an arm, a wrist, a neck, a leg, a torso, and so on) via an attachment member (such as a strap, band, or other attachment member) may operate in at least a connected and a disconnected state. One or more sensors (such as one or more photoplethysmographic sensors, sensorselectrocardiographic sensors, galvanic skin conduction sensors, and so on) located in the wearable device and/or the attachment member may detect the user's body part when present, or may detect that a band or other attachment member is closed or otherwise placed in a connected state. Such detection may be used, in some cases with other data, to switch the wearable device between the connected and disconnected states. In this way, the wearable device may operate in the connected state when worn by a user and in the disconnected state when not worn by the user.

Additionally, the attachment member may have a connected configuration where the attachment member attaches the wearable device to the user's body part and a disconnected configuration where the attachment member may not attach the wearable device to the user's body part. In some implementations, the configuration of the attachment member may be detected and/or a sensor may determine whether or not the user's body part is detected when the attachment member transitions from the disconnected to the connected configuration. Similarly, if the wearable device is operating in the connected state and the attachment member transitions from the connected configuration to the disconnected configuration, the wearable device may switch to the disconnected state. In this way, the operational state of the wearable device may be dependent on whether or not the wearable device is worn by the user while requiring less frequent detection of the user's body part using the sensor(s).

In some such implementations, if the wearable device is operating in the connected state and the attachment member transitions from the connected configuration to the disconnected configuration, the wearable device may not immediately switch to the disconnected state. Instead, upon such transition, it may determine whether or not the sensor detects the user's body part. Then, if the user's body part is not detected, the wearable device may switch to the disconnected state. In this way, the user may be able to transition the attachment member to the disconnected configuration without switching the operational state of the wearable device if the user does not remove the wearable device from his or her body part.

In various cases, determination that the attachment member has transitioned between the connected and disconnected configurations may be performed based on measured conductance or current flow between two or more contacts located in the wearable device and/or the attachment member. For example, the attachment member may include multiple portions that are coupleable to each other. When these portions are coupled, conductive elements (such as conductive metal elements, conductive carbon elements, and/or other types of conductive elements) included within the portions, on the portions, forming the portions, or as connection mechanisms operable to couple the portions (such as conductive wires or traces, conductive coatings, and/or other conductive components) may be positioned relatively near to one another, such that the capacitance or conductance between the contacts may be high. However, when these portions are not coupled, the conductive elements may not electrically connect the contacts such that the conductance between the contacts may be low. Such conductance may be measured by the wearable device and/or wired and/or wirelessly reported to the wearable device.

In some cases, the attachment member or the wearable device may include a proximity sensor which may be utilized to determine when the device and the attachment member have transitioned between connected and disconnected configurations.

In some cases, the attachment member may include multiple portions that are coupleable to each other utilizing two or more magnetic elements. In such cases, a Hall effect sensor or similar sensor may be utilized to determine when the magnetic elements are attracting each other, and thus coupling the portions in the connected configuration, and/or when they are not, thus not coupling the portions in the disconnected configuration. Determination of whether the attachment member is in the disconnected or connected configuration may be based on measurements by the Hall effect sensor.

In various cases, the attachment member may include a single portion that may be stretched in response to applied force and return to an original shape when the force is no longer applied such that it can be positioned onto the user's body part and/or removed from the user's body part. The attachment member may include multiple capacitive elements that are relatively closer to each other when the attachment member is unstretched and further from each other when the attachment member is stretched, thus altering the capacitance between the capacitive elements. As such, the attachment member may be in the connected or disconnected configuration when unstretched and the exact configuration that the attachment member is in may be the reverse of the configuration the attachment member was in before the attachment member was last stretched and allowed to return to original shape. Thus, the configuration of the attachment member may be transitioned each time that the capacitance decreases and then increases, corresponding to stretching and returning to the original shape of the attachment member.

Alternatively, in some cases, the configuration of the attachment member may be determined based on whether or not the sensor detects the body part of the user after the capacitance decreases and then increases. For example, if capacitance decreases and then increases and the sensor then does not detect the user's body part, the attachment member may be determined to be in the disconnected configuration. Similarly, if capacitance decreases and then increases and the sensor then does detect the user's body part, the attachment member may be determined to be in the connected configuration.

In various implementations, the wearable device may authenticate the user while operating in the connected state. Such authentication may include receiving one or more biometrics (such as one or more fingerprints received via a touch sensor, photoplethysmographic information received via a photoplethysmographic sensor, electrocardiographic (ECG) information received via ECG electrodes, and/or other such biometrics), user identifiers, passwords, personal identification numbers, or other such authentication mechanisms received via one or more input/output components. In such cases where the wearable device has authenticated the user while operating in the connected state, the wearable device may determine that the user is no longer authenticated when switching to the disconnected state. In this way, the user's authentication may not continue when the wearable device is no longer subject to the user's immediate control, i.e. is no longer worn by the user.

FIG. 1 is an isometric view of a system 100 for operating a wearable device 103 dependent on whether or not the wearable device is worn. As illustrated in FIG. 1, the wearable device is a heart rate monitor including a touch screen display 104 that is wearable by a user by connecting an attachment member strap 102 to the user's bicep 101. The wearable device may operate in a connected state when attached to the user's bicep and in a disconnected state when detached from the user's bicep.

However, it is understood that this is an example and is not intended to be limiting. In various implementations, the wearable device 103 may be any kind of wearable device that attaches to one or more body parts of a user via one or more attachment members 102.

The wearable device 103 may include one or more components that are not shown. Such components may include one or more processing units, one or more sensors, one or more input/output components, and one or more non-transitory storage media (which may take the form of, but is not limited to, a magnetic storage medium; optical storage medium; magneto-optical storage medium; read only memory; random access memory; erasable programmable memory; flash memory; and so on). The processing unit may execute instructions stored in the non-transitory storage medium to perform one or more wearable device functions. Such functions may include operating in a connected or disconnected state, switching between states, determining when a sensor detects a user's body part, determining whether an attachment member is in a connected or disconnected configuration, receiving user input, authenticating a user, and/or other such operations.

The wearable device may be one of any of a variety of devices. For example, the wearable device may be a health monitor, exercise or other activity monitor, device capable of telling time, device capable of measuring a biometric parameter of a wearer or user, and so on. The device may encircle a portion of a user's body, or may have a strap or band that encircles a part of a user's body. The device may be worn directly by the user, for example as a pair of glasses. The device may be adjacent to or touching a portion of a user's body when worn.

Figure 2A:
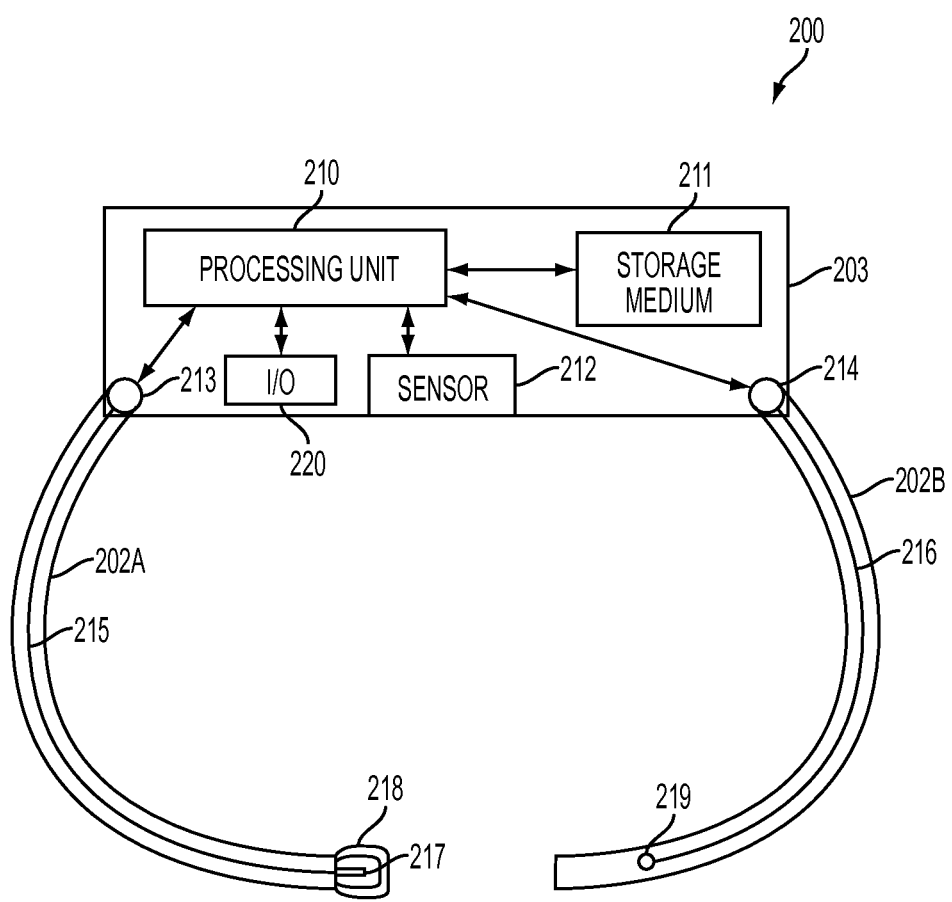
FIG. 2A is a block diagram illustrating the relationships of components of a first embodiment of a wearable device that operates dependent on whether or not the wearable device is worn.

FIG. 2A is a block diagram illustrating the relationships of components of a first embodiment of a wearable device 203 that operates dependent on whether or not the wearable device is worn. In this embodiment, the wearable device includes a processing unit 210, a non-transitory storage medium 211, an input/output component 220 (which may be one or more of any kind of input output component such as a touch sensor, a touch screen, one or more buttons, a keyboard, a biometric sensor, a display, a speaker, a microphone, and so on), one or more sensors 212 for detecting a user's body part (such as one or more photoplethysmographic sensors, proximity sensors, or electrical contacts), and first and second contacts 213 and 214. Also in this embodiment, an attachment member for attaching the wearable device to a user's body part may include a first portion 202A and a second portion 202B, conductive elements 215 and 216, and a connection mechanism including a conductive buckle prong 217, a buckle frame 218, and conductive hole 219.

Figure 2B:
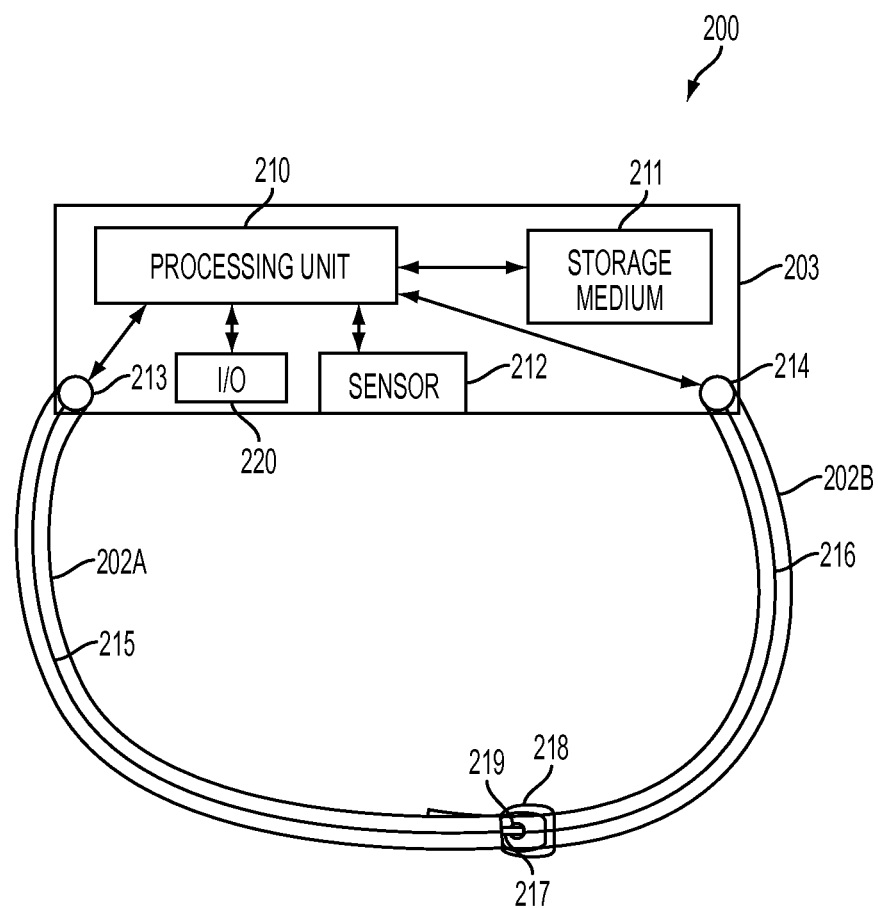
FIG. 2B illustrates the first embodiment of a wearable device of FIG. 2A with the attachment member in a connected configuration.

As illustrated in FIG. 2A, the first and second portions 202A and 202B of the attachment member may be in a disconnected configuration. FIG. 2B illustrates the first embodiment of a wearable device of FIG. 2A with the attachment member in a connected configuration. As illustrated in FIGS. 2A and 2B, the first portion 215 may be coupled to the second portion 216 by inserting the second portion into the buckle frame 218 and inserting the conductive buckle prong 217 into the conductive hole 219. This may result in the connected configuration shown in FIG. 2B. Similarly, the first portion may be uncoupled from the second portion by removing the conductive buckle prong from the conductive hole and removing the second portion from the buckle frame. This may result in the disconnected configuration shown in FIG. 2A.

As the conductive element 215 is conductively connected to the first contact 213 and the buckle prong 217 and the conductive element 216 is conductively connected to the second contact 214 and the conductive hole 219, the first and second contacts may be conductively connected (via the conductor elements conductively coupled via the conductive buckle prong and the conductive hole) when the first and second portions are in the connected configuration and conductively disconnected when the first and second portions are in the disconnected configuration. Thus, the configuration of the first and second portions of the attachment member may be determined by monitoring the conductance between the first and second contacts.

The wearable device 203 may operate in at least either the connected or disconnected state. When the wearable device is in the disconnected state and determines that the first and second portions 202A and 202B of the attachment member transition from the disconnected configuration to the connected configuration, the wearable device may determine whether or not the sensor 212 detects the user's body part. If so, the wearable device may be currently worn and may switch to the connected state. If not, the wearable device may remain in the disconnected state (though in some cases the sensor may periodically attempt to detect the user's body part and the wearable device may switch to the connected state if the user's body part is detected). Similarly, when the wearable device is in the connected state and determines that the first and second portions transition from the connected configuration to the disconnected configuration, the wearable device may switch to the disconnected state (though in some cases the wearable device may first determine that the sensor does not detect the user's body part after the transition before switching operational states, periodically monitoring the sensor in some cases if the sensor does detect the user's body part after the transition).

The wearable device may authenticate the user while operating in the connected state. Such authentication may include receiving one or more biometrics, user identifiers, passwords, personal identification numbers, or other such authentication mechanisms received via the input/output component 220. In such cases where the wearable device has authenticated the user while operating in the connected state, the wearable device may determine that the user is no longer authenticated when switching to the disconnected state.

Conductive elements 215 and 216 are shown in FIGS. 2A and 2B as one or more wires positioned inside the first and second portions 202A and 202B. However, it is understood that this is an example and that various implementations are possible without departing from the scope of the present disclosure. In various implementations, the conductive elements may be any kind of conductive material (such as conductive metal, conductive carbon, and so on) formed in wires or traces within or on the first and/or second portion, formed as coatings on one or more surfaces of the first and/or second portion, and/or other such conductive material arrangements that are operable to conductively connect the first and second contacts 213 and 214 when the first and second portions are connected. For example, in some cases the first and second portions may be formed of conductive material and may thus be the conductive elements.

Further, although the sensor 212 and the first and second contacts 213 and 214 are shown as positioned within the wearable device 203, it is understood that this is an example. In one or more implementations, one or more such components may be located in the attachment member. Additionally, though the wearable device is described as monitoring the conductance between the first and second contacts and whether or not the sensor detects the user's body part, it is understood that in various implementations the attachment member may perform one or more of these functions and report to the wearable device through one or more wired or wireless communication connections. In some implementations, one or more of the first and second contacts may be electrically isolated from the wearable device.

Although the attachment member is shown and described above as including first and second portions 202A and 202B that are coupleable utilizing a buckle configuration connection mechanism, it is understood that this is an example. In various implementations, the attachment member may include any number of portions that are coupleable with or without connection mechanisms. For example, in one or more implementations the attachment member may include a single portion with one or more ends with one or more insertion tabs that are insertable into apertures in the wearable device to place the attachment member into a connected configuration. Such an insertion tab may be conductive and may conductively connect first and second contacts positioned within the aperture.

Further, although the conductive buckle prong 217 and the conductive hole 219 of the connection mechanism are shown and described above as aiding in conductively connecting the first and second contacts 213 and 214, it is understood that this is an example. In some cases the conductive elements 215 and 216 may conductively connect directly in the connected configuration (such as where the first portion 202A has a conductive under side coating that overlaps a conductive top side coating on the second portion 202B when the two portions are coupled) and one or more connection mechanisms may physically couple the first and second portions. Other configurations of components are possible and contemplated.

Moreover, although the connection mechanism is shown and described above as forming a buckle configuration including a conductive buckle prong 217, a buckle frame 218, and conductive hole 219, it is understood that this is an example. In various implementations, any kind of connection mechanism such as a magnetic connection mechanism, a snap connection mechanism, and/or any other kind of mechanism operable to couple the first and second portions 202A and 202B.

Additionally, though this implementation is shown and described above as monitoring the conductance between first and second contacts 213 and 214, it is understood that this is an example. In various cases, the conductance between any number of different contacts may be monitored without departing from the scope of the present disclosure. For example, the first and second contacts 213 and 214 may be embedded in the sensor 212 to measure the galvanic skin conductance between these contacts when the device is attached to a body part, thus eliminating the need for the conductive elements 215, 216, 217, 218, and 219.

Figure 3A:
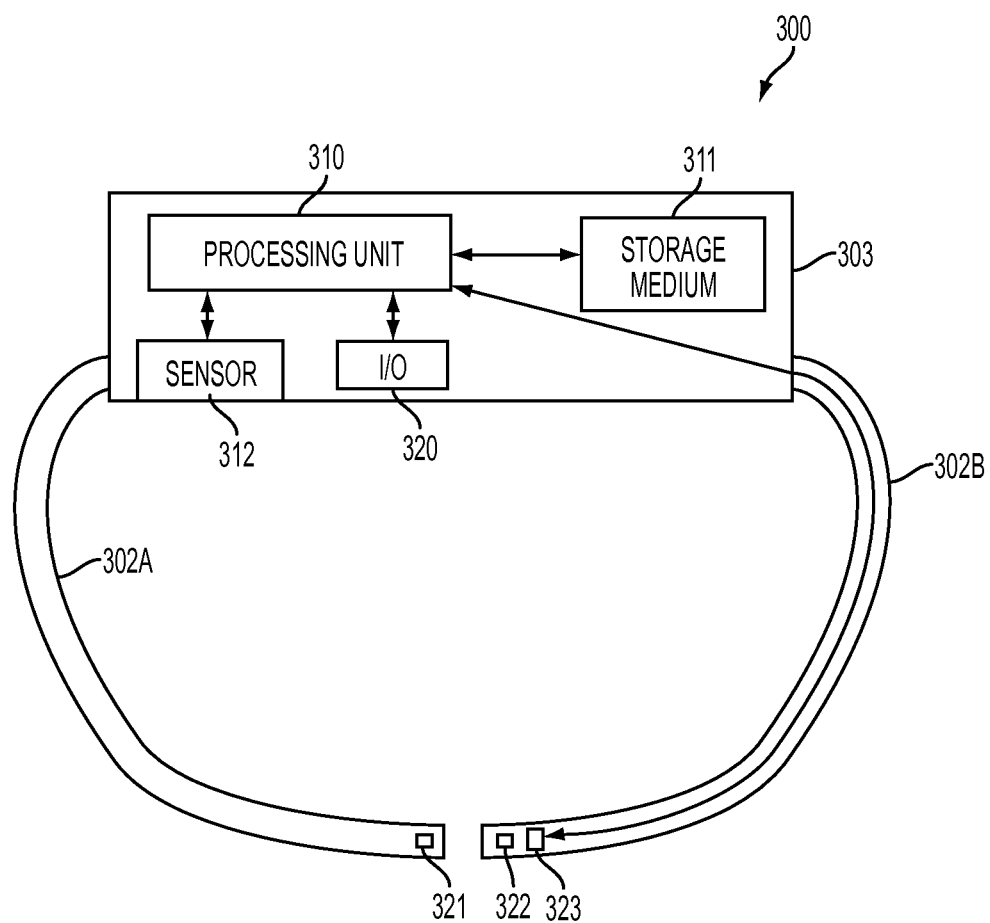
FIG. 3A is a block diagram illustrating the relationships of components of a second embodiment of a wearable device that operates dependent on whether or not the wearable device is worn.

FIG. 3A is a block diagram illustrating the relationships of components of a second embodiment of a wearable device 303 that operates dependent on whether or not the wearable device is worn. Similar to the first embodiment discussed with respect to FIGS. 2A and 2B, the wearable device 303 may include one or more processing units 310, non-transitory storage media 311, sensors 312, and input/output components 320 and the attachment member may include first and second portions 302A and 303B that are coupleable (shown coupled in a connected configuration in FIG. 3B and uncoupled in a disconnected configuration in FIG. 3A).

However, unlike the first embodiment discussed with respect to FIGS. 2A and 2B, the wearable device 303 may not include first and second contacts and the first and second portions 302A and 302B of the attachment member may not include conductive elements. In this second embodiment, the attachment member may include a connection mechanism formed by first and second magnetic elements 321 and 322, located in the first and second portions respectively. When the first and second portions are brought together, the first and second magnetic elements may attract each other, coupling the first and second portions to transition to the connected configuration shown in FIG. 3B. Conversely, when the first and second portions are in the connected configuration and are separated, the attraction between the first and second magnetic elements may be broken and may no longer attract each other, uncoupling the first and second portions to transition to the disconnected configuration shown in FIG. 3A.

The attachment member may also include a hall effect sensor 323 or other sensor operable to detect the magnetic field of the first and/or second magnetic elements 321 and 322 and communicably connected to the processing unit 310. As such, by measuring the differences in the magnetic field, the processing unit may be able to determine whether or not the first and second magnetic elements are attracting each other and thus whether or not the attachment member is in the connected configuration or the disconnected configuration.

Figure 3B:
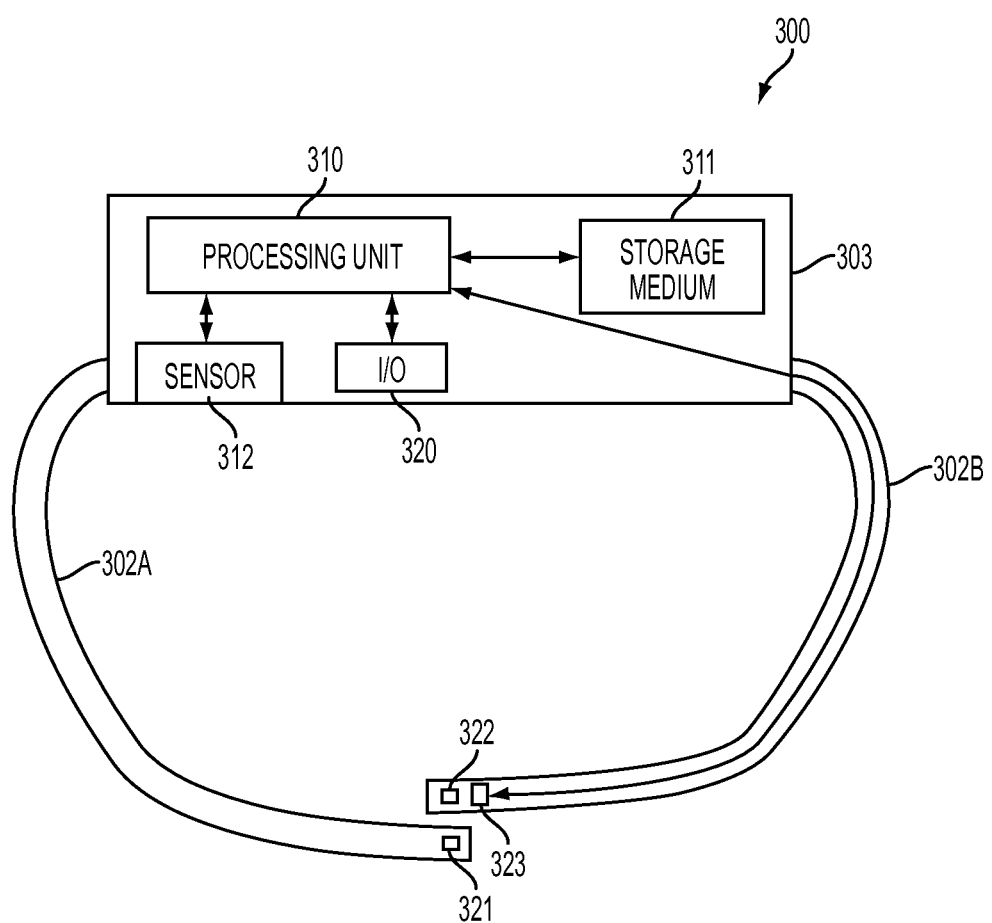
FIG. 3B illustrates the second embodiment of a wearable device of FIG. 3A with the attachment member in a connected configuration.

Although the second embodiment shown in FIGS. 3A and 3B is illustrated and described above as including a particular configuration of particular components, it is understood that this is an example. In various implementations, any number of magnetic elements, hall effect sensors or other sensors (located in the first and/or second portions 302A and 302B and/or the wearable device 303, and/or other components may be utilized without departing from the scope of the present disclosure.

Figure 4A:
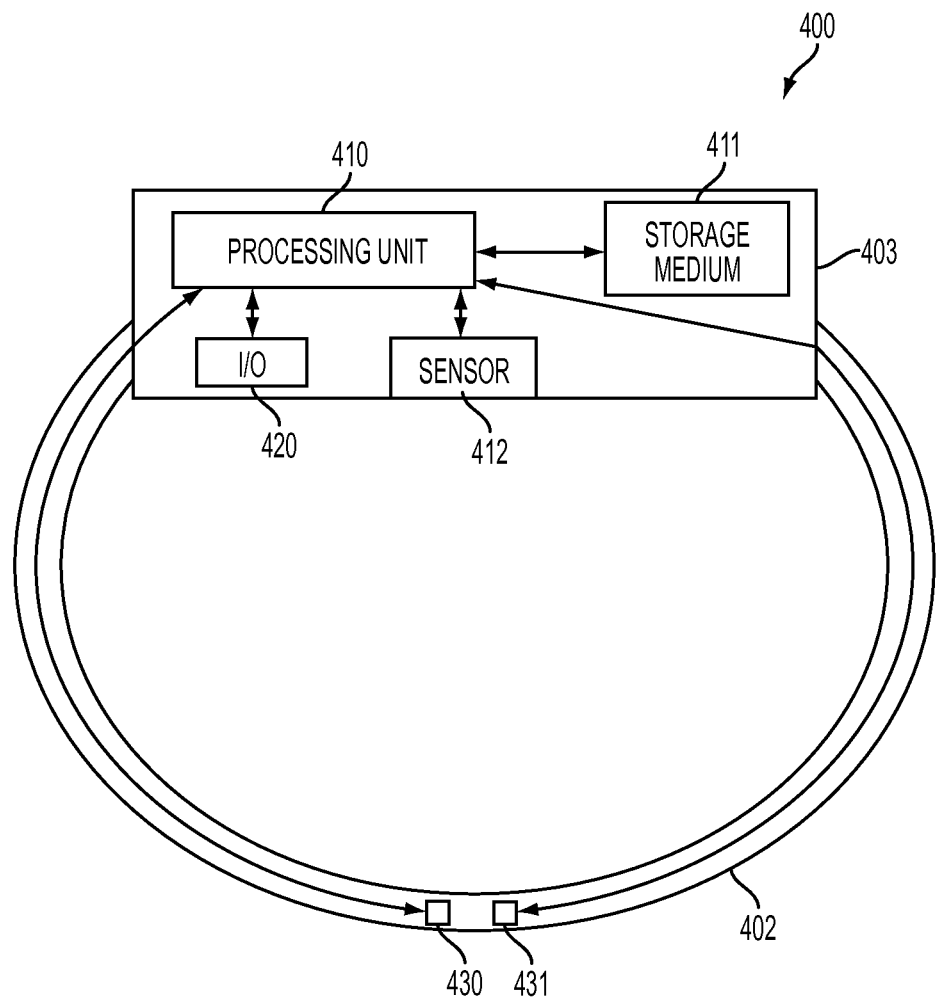
FIG. 4A is a block diagram illustrating the relationships of components of a third embodiment of a wearable device that operates dependent on whether or not the wearable device is worn.

FIG. 4A is a block diagram illustrating the relationships of components of a third embodiment of a wearable device 403 that operates dependent on whether or not the wearable device is worn. Similar to the first embodiment discussed with respect to FIGS. 2A and 2B, the wearable device 403 may include one or more processing units 410, non-transitory storage media 411, sensors 412, and input/output components 420.

Figure 4B:
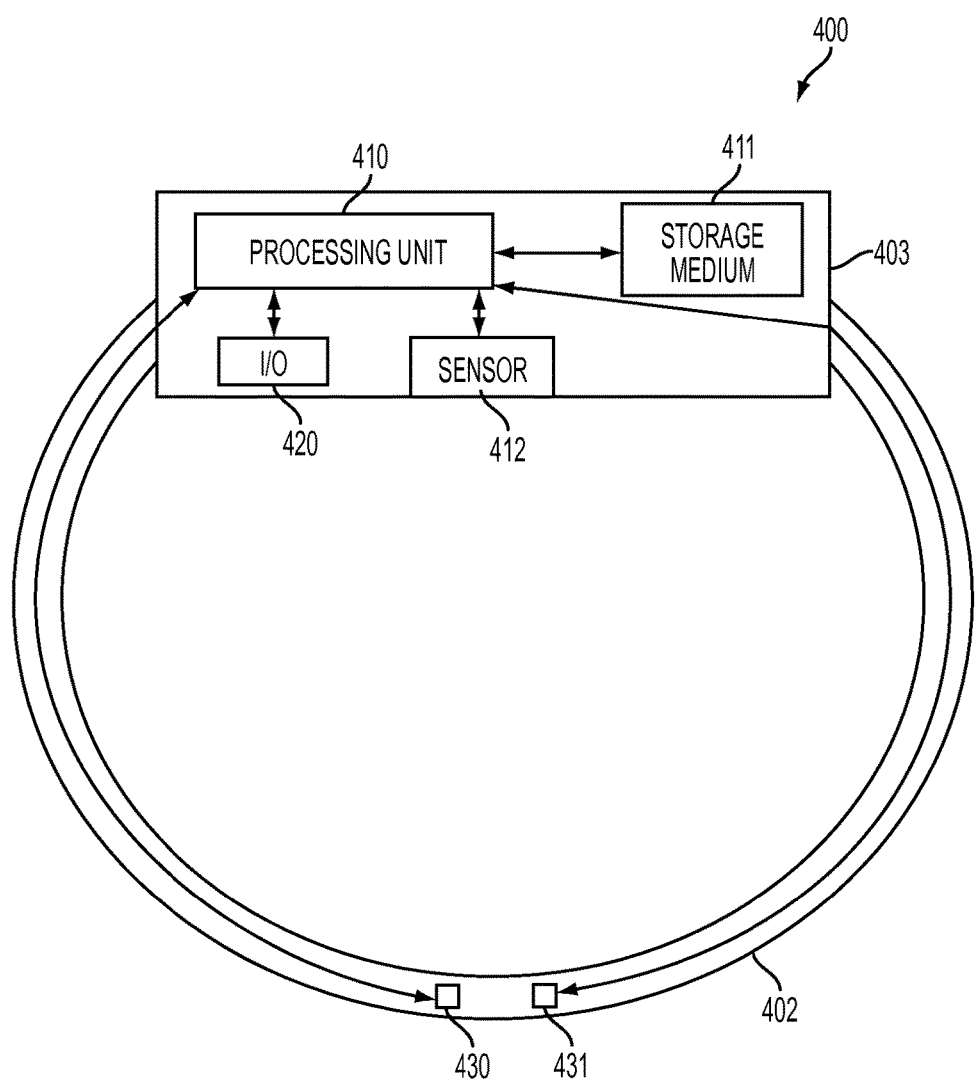
FIG. 4B illustrates the third embodiment of a wearable device of FIG. 4A with the attachment member in a stretched position.

However, unlike the first embodiment discussed with respect to FIGS. 2A and 2B, the wearable device 403 may not include first and second contacts and the attachment member 402 may not include conductive elements. In this second embodiment, the attachment member may be a single portion that may be stretched in response to applied force (as shown in FIG. 4B) and return to an original shape (as shown in FIG. 4A) when the force is no longer applied such that it can be positioned onto the user's body part and/or removed from the user's body part The attachment member 402 may include first and second capacitive elements 430 and 431 that are communicably connected to the processing unit 410 and are relatively closer to each other when the attachment member is unstretched (FIG. 4A) and further from each other when the attachment member is stretched (FIG. 4B), thus altering the capacitance between the capacitive elements. As such, the attachment member may be in the connected or disconnected configuration when unstretched and the exact configuration that the attachment member is in may be the reverse of the configuration the attachment member was in before the attachment member was last stretched and allowed to return to original shape. Thus, the configuration of the attachment member may be transitioned each time that the capacitance decreases and then increases, corresponding to stretching and returning to the original shape of the attachment member.

Alternatively, in some cases, the configuration of the attachment member 402 may be determined based on whether or not the sensor 412 detects the body part of the user after the capacitance decreases and then increases. For example, if capacitance decreases and then increases and the sensor then does not detect the user's body part, the attachment member may be determined to be in the disconnected configuration. Similarly, if capacitance decreases and then increases and the sensor then does detect the user's body part, the attachment member may be determined to be in the connected configuration.

Although the third embodiment shown in FIGS. 4A and 4B is illustrated and described above as including a particular configuration of particular components, it is understood that this is an example. In various implementations, any number of capacitive elements located at various positions in the attachment member 402 and/or the wearable device 403 may be utilized without departing from the scope of the present disclosure.

Figure 5A:
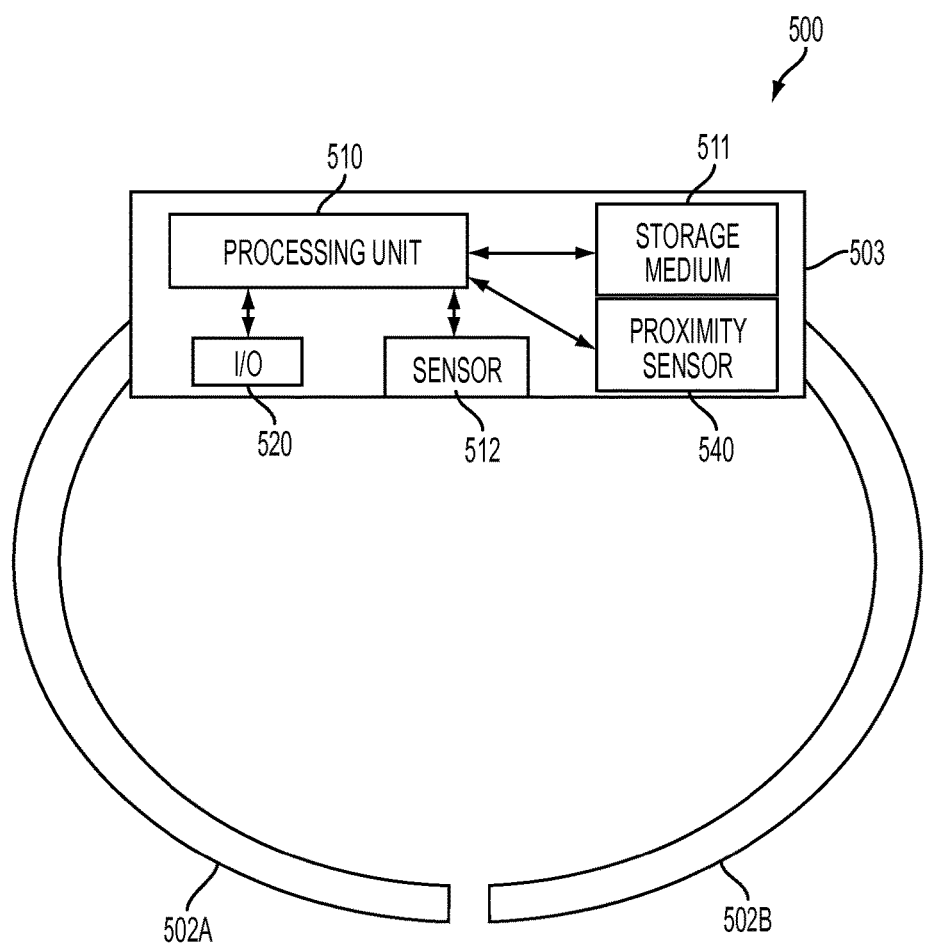
FIG. 5A is a block diagram illustrating the relationships of components of a fourth embodiment of a wearable device that operates dependent on whether or not the wearable device is worn.

FIG. 5A is a block diagram illustrating the relationships of components of a fourth embodiment of a wearable device 503 that operates dependent on whether or not the wearable device is worn. Similar to the first embodiment discussed with respect to FIGS. 2A and 2B, the wearable device 503 may include one or more processing units 510, non-transitory storage media 511, sensors 512, and input/output components 520. In addition, the wearable device or the attachment member may include a proximity sensor 540.

However, unlike the first three embodiments discussed with respect to FIGS. 2A-4B, the wearable device 503 may not include first and second contacts and the attachment member 502A and 502B may not include conductive elements.

In the fourth embodiment, instead of measuring conductance between the first and second contacts 213 and 214, either through the first and second parts 202A and 202B of FIG. 2A-2B or directly through the skin of the user, a proximity sensor embedded in the wearable device or in the first or second parts 502A and 502B can be used to detect the connected and disconnected configurations of the device and the attachment member. When the proximity sensor detects proximity to an object this may be equivalent to detecting the connected configuration and when it does not detect proximity to an object this may be equivalent to detecting the disconnected configuration. The proximity sensor may be used to substitute the connected or unconnected configuration detection based on conductance with a detection based solely on the proximity sensor.

Alternatively, in some cases, the connected or unconnected configuration of the attachment member 502A-502B may be determined based on whether or not the sensor 512 detects the body part of the user. For example, if the proximity sensor 540 detects proximity to an object and the body sensor 512 then does not detect the user's body part, the attachment member may be determined to be in the disconnected configuration. Similarly, if the proximity sensor 540 detects proximity to an object and the body sensor 512 then does detect the user's body part 550 as illustrated in FIG. 5B, the attachment member may be determined to be in the connected configuration.

Figure 5B:
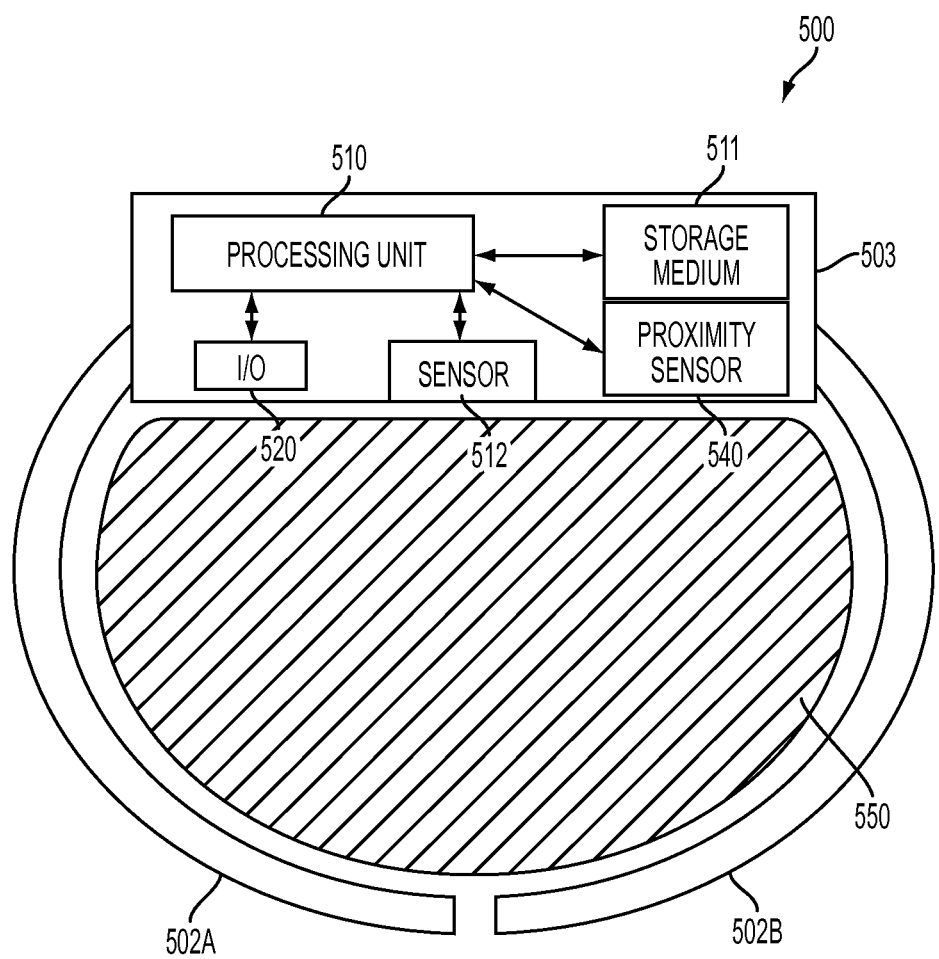
FIG. 5B illustrates the fourth embodiment of a wearable device of FIG. 5A with the attachment member in a connected configuration

Although the fourth embodiment shown in FIGS. 5A and 5B is illustrated and described above as including a particular configuration of particular components, it is understood that this is an example. In various implementations, the detection based on proximity sensor may be used to re-enforce rather than substitute the detection based on conductance. In various implementations, any number of proximity sensors located at various positions in the attachment member 502A-502B and/or the wearable device 503 may be utilized without departing from the scope of the present disclosure.

Figure 6:
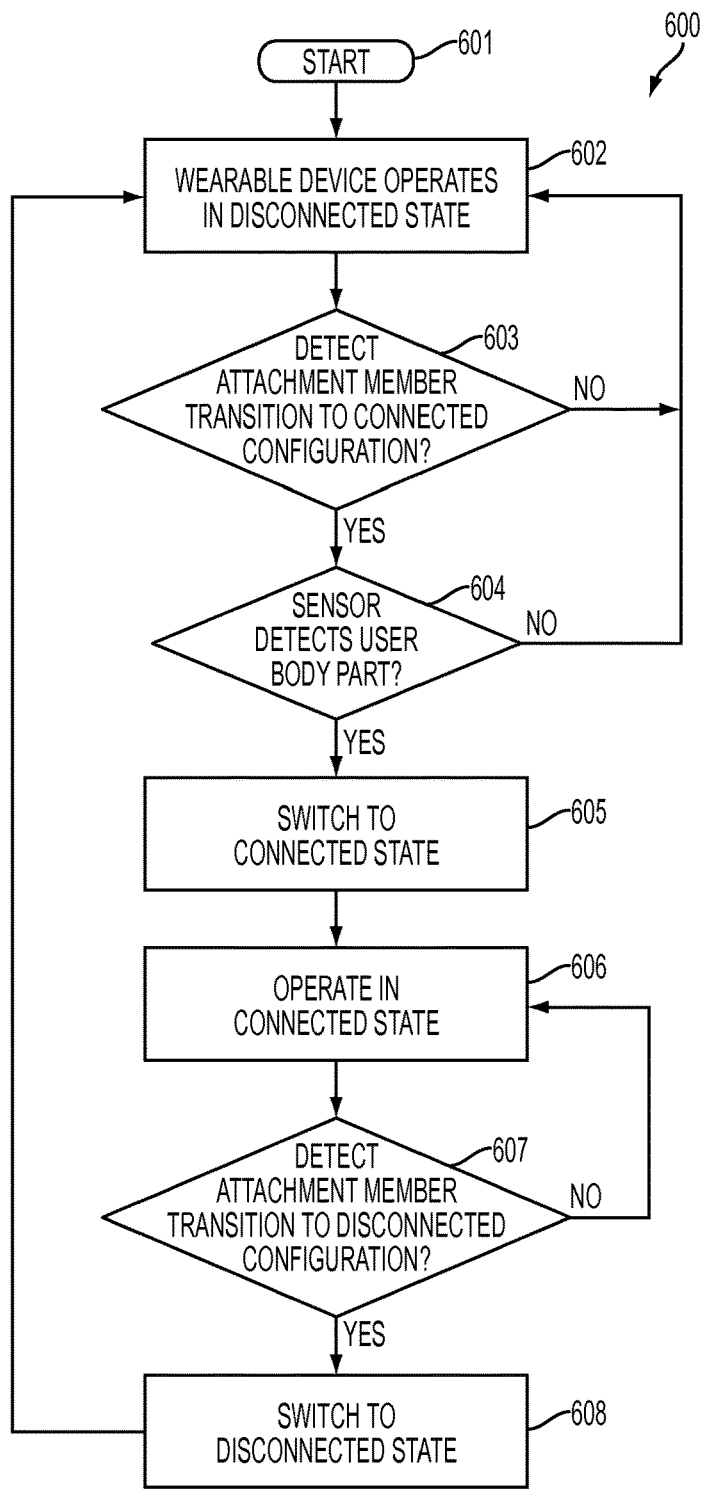
FIG. 6 is a flow chart illustrating an example method for operating a wearable device dependent on whether or not the wearable device is worn. This method may be performed by the system of FIG. 1 and/or the wearable devices of FIGS. 2A-5B.

FIG. 6 is a flow chart illustrating an example method for operating a wearable device dependent on whether or not the wearable device is worn. This method may be performed by the system 101 of FIG. 1 and/or the wearable devices 203-503 of FIGS. 2A-5B.

The flow begins at block 601 and proceeds to block 602 where a wearable device may operate in the disconnected state. The flow then proceeds to block 603 where it may be determined whether or not an attachment member that is operable to attach the wearable device to a body part of a user transitions from a disconnected configuration to a connected configuration. If so, the flow proceeds to block 604. Otherwise, the flow returns to block 602 where the wearable device may continue to operate in the disconnected state At block 604, after it is determined that the attachment member has transitioned from the disconnected configuration to the connected configuration, it may be determined whether or not a sensor detects the body part of the user. If so, the flow proceeds to block 605. Otherwise, the flow returns to block 602 where the wearable device may continue to operate in the disconnected state At block 605, after it is determined that the sensor detects the body part of the user, the wearable device may switch to the connected state. The flow then proceeds to block 606 where the wearable device operates in the connected state. Such operation in the connected state may include authentication of the user. The flow may then proceed to block 607.

At block 607, it may be determined whether or not the attachment member transitions from the connected configuration to the disconnected configuration. If so, the flow proceeds to block 608. Otherwise, the flow returns to block 606 where the wearable device continues to operate in the connected state.

At block 608, after it is determined that the attachment member has transitioned from the connected configuration to the disconnected configuration, the wearable device switches to the disconnected state. In cases where operation in the connected state included authentication of the user, switching to the disconnected state may determine that the user is no longer authenticated. The flow then returns to block 602 where the wearable device operates in the disconnected state.

Although the example method 600 is illustrated and described as including particular operations performed in a particular order, it is understood that this is an example. In various implementations, various orders and arrangements of the same, similar, and/or different operations may be performed without departing from the scope of the present disclosure.

By way of a first example, the example method 600 is illustrated and described as switching the wearable device to the disconnected state from the connected state if the attachment member transitions from the connected configuration to the disconnected configuration. However, in various implementations when the attachment member transitions from the connected configuration to the disconnected configuration it may first be determined that the sensor does not detect the user's body part before transitioning to the disconnected state. In this way, the wearable device may not switch to the disconnected state if the user switches the attachment member to the disconnected state but does not remove the wearable device from the user's body part. In such cases, the sensor may be monitored periodically until the sensor no longer detects the user's body part.

By way of a second example, the example method 600 is illustrated and described as beginning with the wearable device operating in the disconnected state and switching to the connected state when the wearable device is attached to a user's body part. However, in various implementations the method may begin with the wearable device operating in the connected state and switching to the disconnected state when the wearable device is detached from a user's body part.

By way of a third example, the example method 600 is illustrated and described as switching to the connected state from the disconnected state if the attachment member transitions from the disconnected configuration to the connected configuration. However, in various implementations the sensor may detect the user's body part while the wearable device is operating in the disconnected state. In such an example, the wearable device may then switch to the connected state. In some cases, the attachment member may not transition between connected and disconnected configurations.

By way of a fourth example, the example method 600 is illustrated and described as switching to the disconnected state from the connected state if the attachment member transitions from the connected configuration to the disconnected configuration. However, in various implementations the sensor may no longer detect the user's body part while the wearable device is operating in the connected state. In such an example, the wearable device may then switch to the disconnected state.

As described above and illustrated in the accompanying figures, the present disclosure describes systems, apparatuses, and methods for operating a wearable device dependent on whether or not the wearable device is worn. A wearable device that attaches to a body part of a user via an attachment member may operate in at least a connected and a disconnected state. One or more sensors located in the wearable device and/or the attachment member may detect the user's body part when present. Such detection may only be performed when the attachment member is in a connected configuration and may be used to switch the wearable device between the connected and disconnected states. In this way, the wearable device may operate in the connected state when worn by a user and in the disconnected state when not worn by the user.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

We claim:

1. A system for operating a wearable device, comprising:
   the wearable device that operates in at least a connected state and a disconnected state; and
   an attachment member that attaches the wearable device to a limb of a user, the attachment member comprising:
   an element operative to determine that the attachment member is connected; and
   a sensor that detects the limb of the user; wherein:
   the wearable device switches from the disconnected state to the connected state based on the element determining that the attachment member is connected;
   the wearable device is configured to operate in the connected state when attached to the limb of the user;
   the wearable device is configured to operate in the disconnected state when unattached to the limb of the user;
   the wearable device authenticates the user as a particular user while operating in the connected state; and
   the wearable device allows the user to remain authenticated as the particular user until switching to the disconnected state.

2. The system of claim 1, wherein the attachment member transitions between a disconnected configuration and a connected configuration wherein the attachment member attaches the wearable device to the limb of the user in the connected configuration.

3. The system of claim 2, wherein the wearable device detects when the attachment member transitions from the disconnected configuration to the connected configuration.

4. The system of claim 3, wherein the wearable device determines whether or not the sensor detects the limb of the user while operating in the disconnected state upon detection that the attachment member has transitioned from the disconnected configuration to the connected configuration.

5. The system of claim 3, wherein the wearable device switches from the connected state to the disconnected state upon detection that the attachment member has transitioned from the connected configuration to the disconnected configuration.

6. The system of claim 3, wherein the wearable device switches from the connected state to the disconnected state upon determining that the sensor does not detect the limb of the user.

7. The system of claim 6, wherein the wearable device determines whether or not the sensor detects the limb of the user while operating in the connected state upon detecting that the attachment member has transitioned from the connected configuration to the disconnected configuration.

8. The system of claim 2, wherein the wearable device detects when the attachment member transitions between the disconnected configuration and the connected configuration by measuring conductance between a first contact and a second contact.

9. The system of claim 8, wherein the first contact and the second contact are connected via a conductor element when the attachment member is in the connected configuration and are not connected via the conductor element when the attachment member is in the disconnected configuration.

10. The system of claim 8, further comprising a connection mechanism that connects the first contact to the second contact when the attachment member is in the connected configuration and disconnects the first contact from the second contact when the attachment member is in the disconnected configuration.

11. The system of claim 2, wherein:
    the attachment member includes at least a first capacitive element and a second capacitive element;
    the attachment member stretches when force is applied such that a distance between the first capacitive element and the second capacitive element increases causing a capacitance between the first capacitive element and the second capacitive element to decrease and contracts when the force is no longer applied such that the distance between the first capacitive element and the second capacitive element decreases causing the capacitance between the first capacitive element and the second capacitive element to increase; and
    the wearable device determines that the attachment member has transitioned from the disconnected configuration to the connected configuration after the wearable device has determined that the attachment member is in the disconnected configuration when the capacitance decreases and then increases.

12. The system of claim 11, wherein the wearable device determines that the attachment member has transitioned from the connected configuration to the disconnected configuration after the wearable device has determined that the attachment member is in the connected configuration when the capacitance decreases and then increases.

13. The system of claim 2, wherein:
the attachment member includes a first portion that is coupled to a second portion utilizing a first magnetic element and a second magnetic element in the connected configuration;
the first portion is uncoupled from the second portion in the disconnected configuration; and
the wearable device detects when the attachment member transitions between the disconnected configuration and the connected configuration by measuring a magnetic field of at least the first magnetic element or the second magnetic element utilizing a hall effect sensor.

14. The system of claim 2, wherein the wearable device detects when the attachment member transitions between the disconnected configuration and the connected configuration by evaluating an output of a proximity sensor.

15. The system of claim 1, wherein the sensor comprises at least one of a photoplethysmographic sensor, an electrocardiographic sensor, or a galvanic skin conduction sensor.

16. The system of claim 1, wherein the wearable device requires the user to re-authenticate as the particular user after switching to the disconnected state.

17. The system of claim 1, wherein the wearable device determines the user is no longer authenticated as the particular user after switching from the connected state to the disconnected state.

18. The system of claim 1, wherein the wearable device authenticates the user as the particular user by receiving a biometric of the user, a user identifier, a password, or a personal identification number.

19. A method for operating a wearable device dependent on whether or not the wearable device is worn, the method comprising:
if the wearable device is operating in a disconnected state, determining to switch to a connected state by:
detecting that an attachment member that attaches the wearable device to a limb of a user has been transitioned from a disconnected configuration to a connected configuration;
upon detecting that the attachment member has been transitioned from the disconnected configuration to the connected configuration, detecting the limb of the user utilizing a sensor;
configuring the wearable device to operate in the disconnected state when unattached to the limb of the user;
configuring the wearable device to operate in the connected state when attached to the limb of the user;
authenticating the user as a particular user while operating in the connected state; and
allowing the user to remain authenticated as the particular user until switching to the disconnected state.

20. The method of claim 19, further comprising:
if the wearable device is operating in the connected state, detecting that the attachment member has been transitioned from the connected configuration to the disconnected configuration; and
determining to switch to the disconnected state in response to said operation of detecting that the attachment member has been transitioned from the connected configuration to the disconnected configuration.

21. A wearable device, comprising:
a processing unit that operates in at least a connected state and a disconnected state;
a housing;
an attachment member that attaches the housing to a limb of a user;
an element operative to determine that the attachment member is in a connected configuration around the limb of the user; and
a sensor that detects the limb of the user; wherein:
the processing unit switches from the disconnected state to the connected state based on the element determining that the attachment member is in the connected configuration around the limb of the user;
the processing unit is configured to operate in the connected state when the housing is attached to the limb of the user;
the processing unit is configured to operate in the disconnected state when the housing is unattached to the limb of the user;
the processing unit authenticates the user as a particular user while operating in the connected state; and
the processing unit allows the user to remain authenticated as the particular user until switching to the disconnected state.

* * * * *